United States Patent
Feizbakhsh et al.

(10) Patent No.: US 12,415,020 B2
(45) Date of Patent: Sep. 16, 2025

(54) METHOD AND SYSTEM FOR PRODUCTION OF ANTI-MICROBIAL ORTHODONTIC ELASTOMERIC LIGATURES

(71) Applicants: Masood Feizbakhsh, Esfahan (IR); Amir Sarrafzadeh, Tehran (IR); Zohreh Ghazalbash, Mashhad (IR)

(72) Inventors: Masood Feizbakhsh, Esfahan (IR); Amir Sarrafzadeh, Tehran (IR); Zohreh Ghazalbash, Mashhad (IR)

( * ) Notice: Subject to any disclaimer, the term of this patent is extended or adjusted under 35 U.S.C. 154(b) by 715 days.

(21) Appl. No.: 17/739,914

(22) Filed: May 9, 2022

(65) Prior Publication Data
US 2022/0355000 A1 Nov. 10, 2022

Related U.S. Application Data
(60) Provisional application No. 63/186,140, filed on May 9, 2021.

(51) Int. Cl.
*A61C 7/30* (2006.01)
*A61L 31/16* (2006.01)

(52) U.S. Cl.
CPC .............. *A61L 31/16* (2013.01); *A61C 7/303* (2013.01); *A61L 2300/206* (2013.01); *A61L 2300/404* (2013.01)

(58) Field of Classification Search
CPC ... A61C 7/303; A61L 31/16; A61L 2300/206; A61L 2300/404
USPC .......................................................... 433/11
See application file for complete search history.

(56) References Cited

U.S. PATENT DOCUMENTS

| | | | |
|---|---|---|---|
| 6,203,317 B1* | 3/2001 | Davanathan | A61C 7/303 433/22 |
| 6,267,590 B1* | 7/2001 | Barry | A61C 19/06 433/20 |
| 2004/0167572 A1* | 8/2004 | Roth | A61B 17/12181 606/219 |
| 2004/0197372 A1* | 10/2004 | Llanos | A61F 2/91 424/423 |
| 2009/0104244 A1* | 4/2009 | Flanagan | A61L 31/10 514/291 |
| 2009/0176183 A1* | 7/2009 | Conrad | A61L 27/18 427/2.29 |
| 2009/0226501 A1* | 9/2009 | Parsonage | A61P 35/00 424/423 |
| 2014/0295378 A1* | 10/2014 | Lyngstadaas | A46B 5/02 15/160 |
| 2017/0086944 A1* | 3/2017 | Hulwi | A61C 7/303 |

(Continued)

*Primary Examiner* — Matthew M Nelson
(74) *Attorney, Agent, or Firm* — Nasser Ashgriz; UIPatent Inc.

(57) ABSTRACT

A method for production of anti-microbial orthodontic elastomeric ligatures is disclosed. The elastomeric ligatures are coated with an anti-microbial solution layer by layer. The coating solution comprising an anti-bacterial agent, a polymer and a solvent in the following ratio: 2 g anti-microbial agent, 4 g polymer and 200 mL solvent. The hypo-allergic latex-free orthodontic elastomeric ligatures with an internal diameter of 0.045 inches and external diameter of 0.115 inches are rinsed in distilled water, dried at 60° C. and sprayed with the anti-bacterial solution two times and dried for five minute. This process is repeated for five times and the elastomeric ligatures are dried at room temperature for 1 h.

4 Claims, 6 Drawing Sheets

(56) References Cited

U.S. PATENT DOCUMENTS

2020/0246122 A1* 8/2020 Terry .................... A61K 31/167
2022/0355000 A1* 11/2022 Feizbakhsh ............. A61L 31/10

* cited by examiner

METHOD AND SYSTEM FOR PRODUCTION OF ANTI-MICROBIAL ORTHODONTIC ELASTOMERIC LIGATURES

CROSS REFERENCE TO RELATED APPLICATIONS

This application claims priority to provisional U.S. Patent Application No. 63/186,140, filed on May 9, 2021, entitled "METHOD AND SYSTEM FOR PRODUCTION OF ANTI-MICROBIAL ORTHODONTIC COMPOSITIONS AND APPLIANCES", the aforementioned application being hereby incorporated by reference in its entirety.

FIELD OF THE INVENTION

The present invention relates in general to prevention of dental diseases in orthodontic patients and in specific to a method of producing anti-microbial orthodontic appliances to prevent of caries development.

BACKGROUND OF THE INVENTION

Repositioning teeth for aesthetic or other reasons is accomplished conventionally by wearing what are commonly referred to as "braces." Braces comprise a variety of appliances such as brackets, arch wires, ligatures, and O-rings.

Oral hygiene maintenance is difficult for orthodontic patients due to excessive plaque retention around orthodontic wires and brackets. This often increases the risk of enamel demineralization and dental caries. On the other hand, the speed of demineralization that occurs around fixed orthodontic appliances is higher than the usual speed of development of carious lesions, such that the first clinical manifestations of enamel demineralization often appear within the first 6 months following the initiation of orthodontic treatment.

Long-term fixed orthodontic treatment lasting for 1 or 2 years would cause some changes in the oral microflora. It can increase the proliferation of cariogenic bacteria, cause periodontal irritation and leads to formation of microbial biofilm on the surface of teeth and orthodontic appliances. Streptococcus mutans (S. mutans) is among the most important bacteria involved in caries development. Its mechanism of action is based on the production of organic acids and dissolution of the mineral content of the enamel.

In the recent years, many products were introduced to the market that are capable of releasing antibacterial agents (such as bonding agents releasing fluoride) to prevent or decrease dental caries. However, there is still no evidence to support the claim that fluoride added to bonding agents can prevent demineralization.

The most commonly recommended method by orthodontists to prevent white spot lesions (WSL) formation was the use of a fluoride mouth rinse after brushing. Patients were encouraged to use a fluoride mouth rinse by 85% of orthodontists and 69% of general dentists and 76% of orthodontists recommended in-office fluoride treatment for patients with severe WSLs immediately after orthodontic treatment. This treatment may cause additional problems since use of fluoride treatment after the formation of WSL can result in the formation of fluorapatite crystals which prevents the remineralization of WSLs. Addition of fluoride further may change the physical properties of elastics and may result in their faster degradation in the oral cavity.

Chlorhexidine (CHX) is a cationic biguanide with broad-spectrum antibacterial activity. It is considered as the gold-standard antibacterial agent due to its high potential to inhibit microbial plaque formation. It has both bactericidal and bacteriostatic activities, and is effective against Gram-positive and Gram-negative microorganisms, fungi and viruses. In low concentrations, CHX binds to the bacterial cell membrane and increases its permeability, resulting in leakage of intracellular components including sodium. In high concentrations, it leads to deposition of bacterial cytoplasm and cell death. Products containing CHX are available in the form of mouthwashes, gels, sprays, toothpastes, lozenges, varnishes and sustained-release drug delivery systems (DDSs).

The most important property of CHX is its inherent sustained antimicrobial effect over long periods of time, which is due to the binding of CHX to hydroxyapatites present in the enamel and proteins and glycoproteins present in the saliva and dental plaque, which would result in sustained release of CHX within 12 to 24 hours. However, it should be noted that the saliva flow decreases the sustained antimicrobial activity of products. However, long presence of antibacterial agents in the oral cavity would prevent dental caries during the course of orthodontic treatment.

CHX can prevent dental biofilm formation and decrease the salivary level of Streptococcus mutans (S. mutans), which is the main culprit responsible for development of dental caries. Recently, CHX controlled release systems were introduced to further benefit from its antimicrobial properties. In this regard, CHX DDS were introduced to overcome the clinical complications associated with the conventional use of CHX to decrease the salivary level of S.mutans.

A previous study used CHX-releasing orthodontic elastomeric ligatures for this purpose. In this method, a thick coating of CHX is formed on the surface of elastomeric ligatures. However, preservation of this coating and enabling the sustained release of CHX are among the difficulties encountered in use of this technique.

Attempts have been made to solve various aspects of this problem in the field of orthodontic appliances. For example, Masek et al. [1] showed that the salivary level of Lactobacillus and S. mutans significantly decreased 1 and 2 months after the application of CHX varnish three times a week. The salivary level of bacteria was significantly lower in the test group compared with the control group and after 2 months, the level of bacteria was lower than that at baseline. They suggested that CHX varnish can be applied every 3 months to exert maximum antibacterial effects. Although their methodology was different from the present invention and they used CHX varnish. Their results showed a significant reduction in S. mutans count of the saliva in the test group over time.

Twetman et al. [2] found that application of CHX varnish significantly decreased the level of S. mutans at 1 week and 1 month, but the difference was no longer significant after 3 and 6 months. A systematic review by Tange et al. [3] evaluated the antibacterial effects of CHX varnish on fixed orthodontic patients and concluded that CHX varnish was effective on S. mutans only after 3 to 4 weeks. However, monthly application of CHX varnish is not cost-effective during the 2-year treatment period and is also time consuming.

Liptak et al. [4] assessed the effect of monthly application of CHX gel on S. mutans and Lactobacillus counts in the saliva and plaque during a 6-month period. They reported that the reduction in S. mutans count of dental plaque was significant after 2 months.

The efficacy of fluoride-releasing elastomeric ligatures has been extensively studied in orthodontic patients. Miura et al. [5] reported that use of elastomeric ligatures releasing fluoride in orthodontic patients did not cause a significant change in the count of S. mutans in the saliva or dental plaque. Benson et al. [6] showed that fluoride-releasing elastomers were not clinically effective for reduction of S. mutans count. Addition of fluoride or CHX to elastomeric ligatures seems logical because by doing so, antibacterial agent is easily delivered to the desired site. Also, elastics are constantly replaced and provide a fresh source of antibacterial agent. However, addition of fluoride did not show promising results. Jeon et al. [7,8] further reported that coating of elastics did not affect their physical properties.

Addition of fluoride or CHX to orthodontic bonding agents is another suggested strategy to benefit from their cariostatic and antimicrobial property in orthodontic patients. However, it does not seem ideal since the fluoride release potential would not last long. Some fluoride-containing cements such as glass ionomers have the recharge potential and can not only release, but also uptake fluoride. However, it is not known whether the level of fluoride released by these cements is adequately high during the entire course of orthodontic treatment to prevent WSLs.

In general, the results of adding fluoride to composite resins have not been promising. Despite the cariostatic effects of glass ionomers, they have significantly lower strength than composite resins and have a high rate of debonding. Chung et al. [9] showed that a primer containing CHX had strong antimicrobial activity and did not significantly affect the bond strength. However, CHX-containing adhesives are only applied for bracket bonding, and their antibacterial agent reservoir would not last long; whereas, CHX-releasing elastomeric ligatures are replaced on a monthly basis and provide a fresh source of CHX.

Therefore, there is a need for an effective biocidal agent that both avoid the formation of resistant microbes and can be adapted for use in orthodontic applications which overcome the disadvantages and defects of the prior art.

SUMMARY OF THE INVENTION

The present invention is a method in which the orthodontic elastomeric ligatures are coated with chlorhexidine (CHX) based on a novel layer-by-layer method. In this method Hypo-allergic latex-free orthodontic elastomeric ligatures with an internal diameter of 0.045 inch and external diameter of 0.115 inch are rinsed in distilled water and dried at 60° C. Then a coating solution is sprayed on the ligatures five times. Each time, each side of the wire is sprayed twice. After the first spray, the ligature is dried for 5 min and then is sprayed again.

Since orthodontic elastomeric ligatures are a common site of microbial plaque formation, addition of antibacterial agents to elastomeric ligatures seems logical. By doing so, the antibacterial agent is available where it is most needed. Moreover, elastomeric ligatures are continuously replaced and can serve as a fresh source of antibacterial agent.

Considering the extensive use of elastomeric ligatures in orthodontic treatment, the present invention provides a novel DDS based layer-by-layer technique, which shows successful results in vitro. This innovation shows the effect of using CHX-releasing elastomeric ligatures on the number of S. mutans in the saliva and dental plaque and on elastomeric ligatures in orthodontic patients.

It is therefore an object of the present invention to provide a novel method to produce a sustainable and effective biocidal agent that avoids the formation of resistant microbes and decrease gum inflammation and tooth decay around Orthodontic fix appliances and overcome the disadvantages of the prior art.

BRIEF DESCRIPTION OF THE DRAWINGS

Embodiments herein will hereinafter be described in conjunction with the appended drawings provided to illustrate and not to limit the scope of the claims, wherein like designations denote like elements, and in which:

DETAILED DESCRIPTION OF PREFERRED EMBODIMENTS

Figure 1:
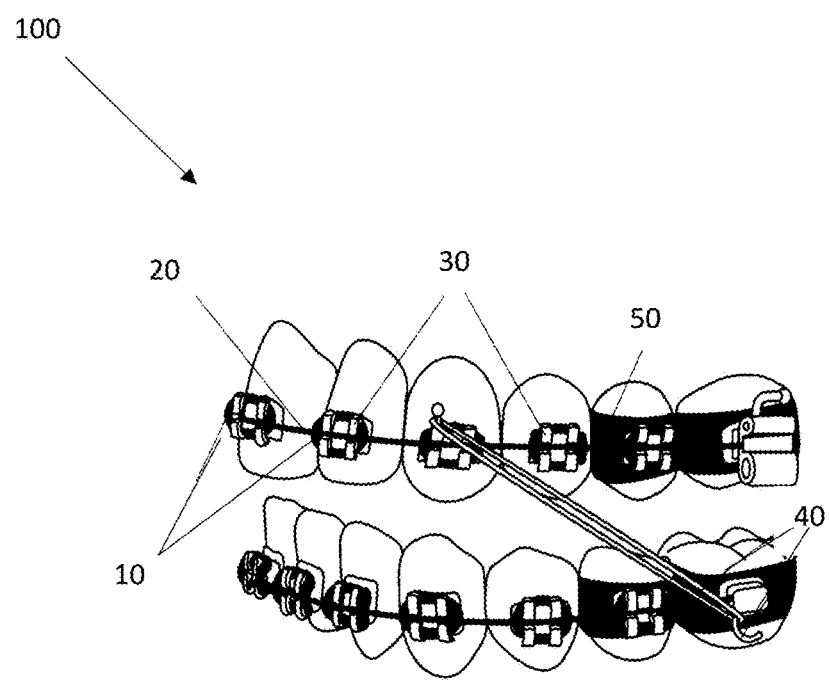
FIG. 1 is a representation of various parts of an orthodontic brace.

As shown in FIG. 1 orthodontic appliance 100 is comprised of orthodontic wires 20 secured on brackets 30 and bands 50 that are bonded onto tooth enamel and are held in position by elastomeric ligature ties 10. Composite and adhesive are used for bracket bonding. The wire 20 is fastened to all of the brackets 30 and creates force to move teeth into proper alignment. Brackets 30 are connected to the bands or directly bonded on the teeth and hold the wire 20 in place. The wire 20 is held to each bracket with a ligature 10. Elastic hooks and rubber bands 40 help move teeth toward their final position.

These appliances encourage colonization of microorganisms around the brackets 30 and elastomeric ligature ties 10. The most common microorganisms that can colonize and cause white spot lesions (WSL) and dental caries on enamel surface are gram-positive Streptococcus mutans (S. mutans). When poor oral hygiene is maintained after fixed orthodontic appliance placement, this can result in formation of WSLs and periodontitis. Development of WSLs is due to prolonged plaque accumulation, which causes the decalcification of enamel. WSLs, if left untreated can progress to dental caries.

Figure 2:
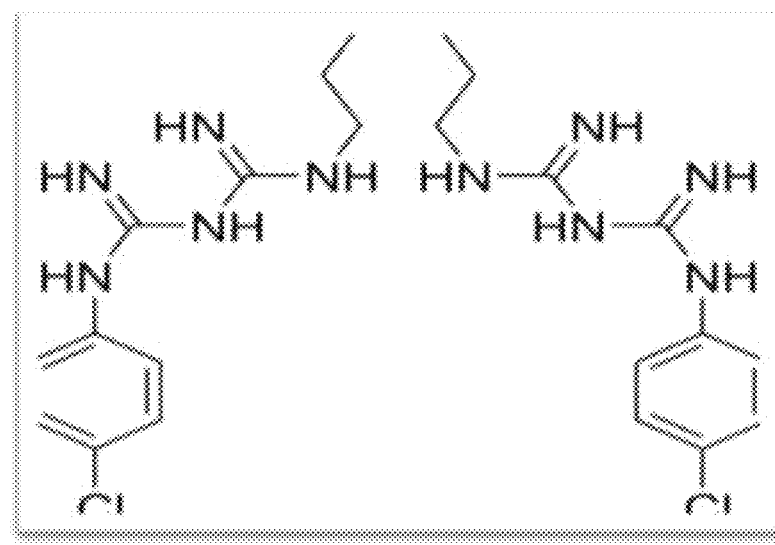
FIG. 2 is a schematic representation of the structural formula of Chlorhexidine (CHX) as an antibacterial agent being used for the coating solution of the present invention.

Prevention of microbial buildup is a preferred alternative to treatment. Chlorhexidine (CHX) is an antimicrobial agent which belongs to the biguanide class of drugs that is efficacious against gram-negative, gram-positive bacteria and yeasts. As a broad-spectrum antimicrobial and antifungal agent, CHX does not promote the development of bacterial resistance and it is widely used in medicine and in dentistry, as a mouth rinse in the form of CHX digluconate. FIG. 2 shows the chemical structure of CHX digluconate.

Figure 3:
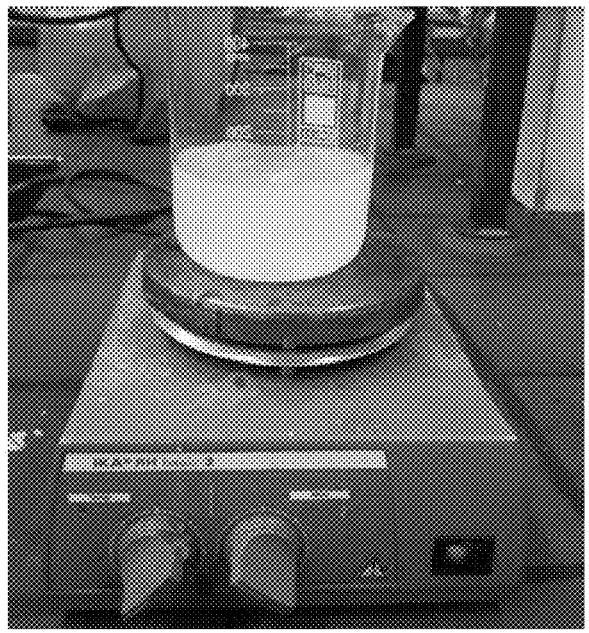
FIG. 3 shows the preparation of the coating solution as an antibacterial agent for the orthodontic ligatures according to the present invention.

According to FIG. 3 for the preparation of the coating solution CHX diacetate (Sigma Aldrich, St. Louis, MO, USA) was used as antibacterial agent and ethyl cellulose (N100; Sigma Aldrich, St. Louis, MO, USA) was used as polymer to prepare the coating solution. The polymer volume was 2% of the solution, and dichloromethane (Duksan Pure Chemicals) was used as solvent in the following ratio: 2 g CHX diacetate+4 g ethyl cellulose+200 mL dichloromethane. First, ethyl cellulose was completely dissolved in dichloromethane solvent using a stirrer for 24 h. Next, CHX diacetate was added to the solution.

Figure 4:
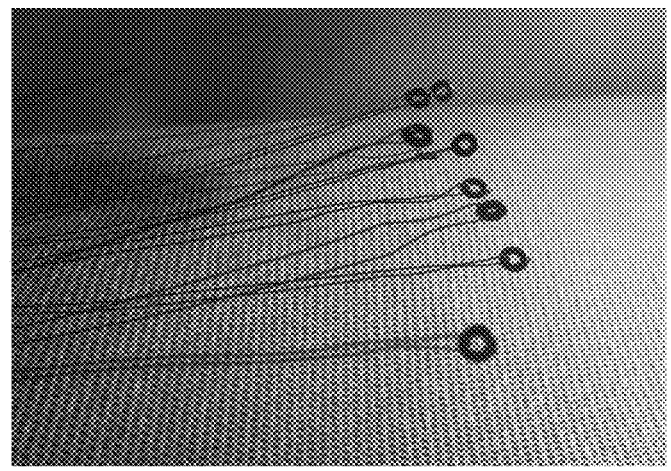
FIG. 4 is an illustration of elastomeric ligatures made of Hypo-allergic latex-free orthodontic elastomeric ligatures to which the coating of the present invention is applied.

According to FIG. 4 for the preparation of elastomeric ligatures, Hypo-allergic latex-free orthodontic elastomeric ligatures with an internal diameter of 0.045 inch and external diameter of 0.115 inch were rinsed in distilled water and dried at 60° C. The coating solution was sprayed on the ligatures five times. Each time, each side of the wire was sprayed twice. After the first spray, the ligature was dried for 5 min and then it was sprayed again. Next, elastomeric ligatures were dried at room temperature for 1 h, and three rings of each type of ligature (CHX-releasing and conventional ligatures) were cultured to ensure absence of *S. mutans*.

The present system and method is tested by using elastomeric ligatures prepared with the method of the present invention in a number of orthodontic patients. A double-blind clinical trial was used to evaluate 30 orthodontic patients between 14 to 25 years, who were randomly divided into two groups. CHX-releasing elastomeric ligatures were used in the test group while the conventional elastomeric ligatures were used for the control group. Saliva samples were collected at baseline, and 7, 14, 21 and 28 days after the intervention. Plaque samples were also collected at baseline and after 28 days. Elastomeric ligatures were collected in both groups after 28 days. The collected samples were cultured to count the number of *S. mutans*. Data were analyzed using the Mann-Whitney and Wilcoxon tests.

The result was that the salivary count of *S. mutans* was significantly lower in the test group at 7, 14, 21 and 28 days ($P<0.05$). The *S. mutans* count on the surface of CHX-releasing ligatures was significantly lower than that on the surface of conventional ligatures ($P<0.05$). However, no significant difference was noted in *S. mutans* count in plaque samples between the two groups ($P>0.05$). The salivary level of *S. mutans* significantly decreased during the course of study in the test group. In conclusion, CHX-releasing elastomeric ligatures can significantly decrease the salivary count of *S. mutans* in orthodontic patients.

In this double-blind clinical trial, sample size was calculated to be 15 in each group considering the minimum difference of 30% between the two groups, 80% study power and 95% confidence interval. A total of 30 patients between 14 to 25 years were selected who required fixed orthodontic treatment. The patients were selected using convenience sampling and received oral hygiene instructions. They were requested to brush their teeth twice a day. They were also asked to floss their teeth. All patients used a toothpaste containing 0.3% sodium fluoride during the study period. The patients were requested to refrain from eating and drinking for 2 h prior to sampling. They were also requested not to use mouthwash during the study period.

The inclusion criteria were (I) presence of all natural teeth, (II) requiring fixed orthodontic treatment, (III) no smoking, (IV) absence of extensive dental restorations or fixed partial dentures, (V) no antibiotic use during the study period and the 2 months prior to the onset of study, (VI) absence of periodontal disease prior to treatment onset, (VII) high motivation for oral hygiene maintenance, (VIII) no use of mouthwash during the study period, (IX) no restoration on the buccal surface of the teeth and (X) normal anatomical shape and height of teeth.

The exclusion criteria were (I) systemic disease or medication intake, (II) history of previous orthodontic treatment, (III) history of CHX use for 1 week or longer in the past 2 months, (IV) presence of active carious lesions, and (V) low saliva flow. The selected 30 patients were randomly divided into test and control groups (n=15).

Figure 5:
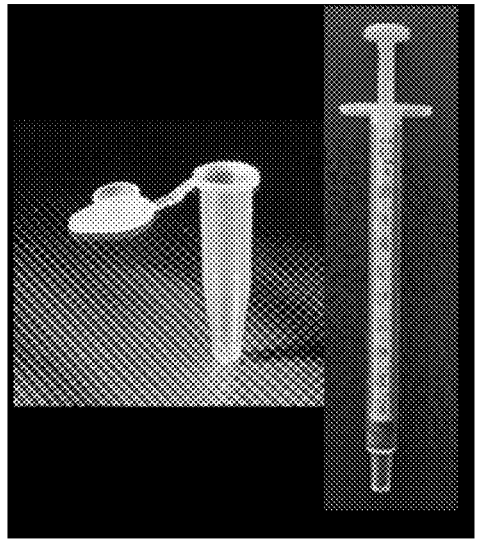
FIG. 5 shows the process of collecting salvia of a patient in a sterile syringe for transferring into micro-tube for S. mutans count.
Figure 6:
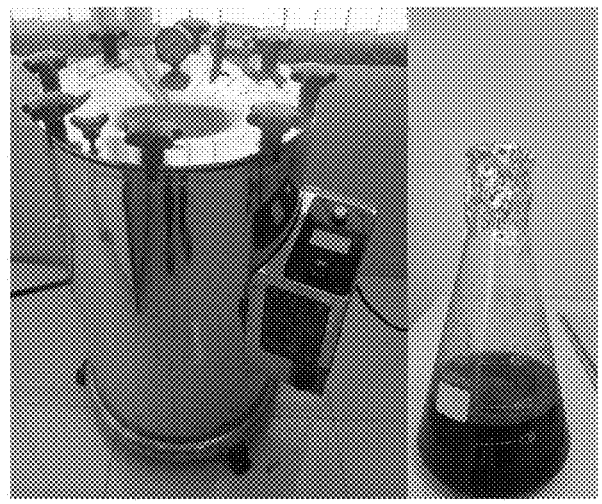
FIG. 6 shows the preparation of the culture medium for the sample processing.

According to FIG. 5 in clinical procedure, in the first visit, baseline saliva samples were collected from both the test and control group patients. The patients were requested not to eat or drink for 2 h prior to sampling. The patients were requested to sit on a dental chair for 5 min, and 0.5 mL of unstimulated saliva was collected using a sterile syringe and transferred into a micro-tube to determine the salivary count of *S. mutans*. Immediately after saliva collection, dental plaque sample was obtained from the second premolar site bilaterally using a sterile periodontal probe.

FIGS. 6 to 9 show the procedure of the sampling implemented in this clinical trial. The plaque sample was transferred into a micro-tube containing 1 mL saline. After sampling, the teeth underwent professional cleaning and the brackets were bonded. Roth brackets with a slot size of 0.022×0.028 inch were used in all patients. A minimum of 20 brackets were used for patients. The same type of composite and adhesive was used for bracket bonding in all patients.

CHX-releasing ligatures were used for patients in the test group while conventional ligatures were used for control patients. The ligatures had similar color coding in both groups. Thus, the patients were blinded to the type of ligatures. The samples were placed next to dry ice and were sent to a microbiology lab in less than 2 h. Saliva samples were collected again at 7, 14, 21 and 28 days after placement of ligatures. On day 28, dental plaque samples were also collected in addition to saliva samples from the same site. Also, elastomeric ligatures were removed from the oral cavity using a sterile explorer and placed in 1 mL of saline and sent to the microbiology lab.

Figure 7:
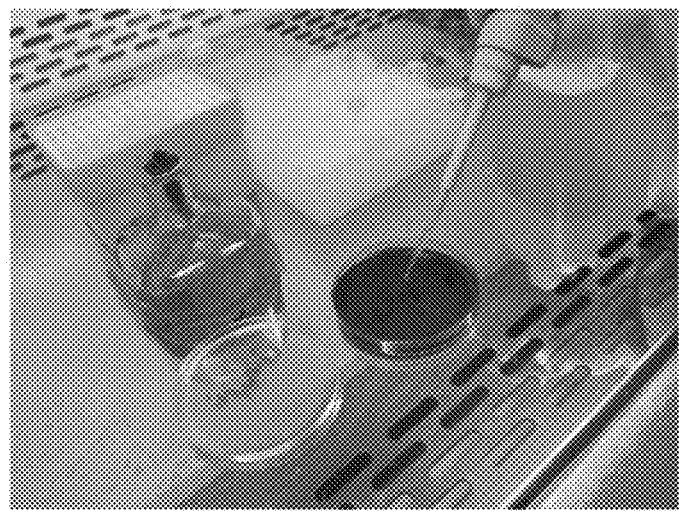
FIG. 7 shows the culture medium poured into sterile plates after mixing the solution.
Figure 8:
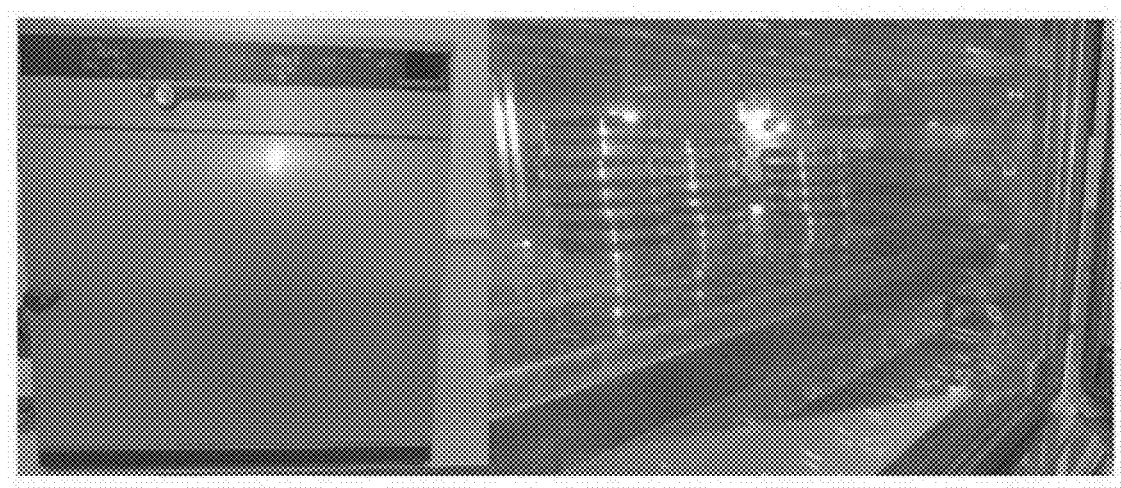
FIG. 8 shows the samples placed into the incubator for centrifuging.
Figure 9:
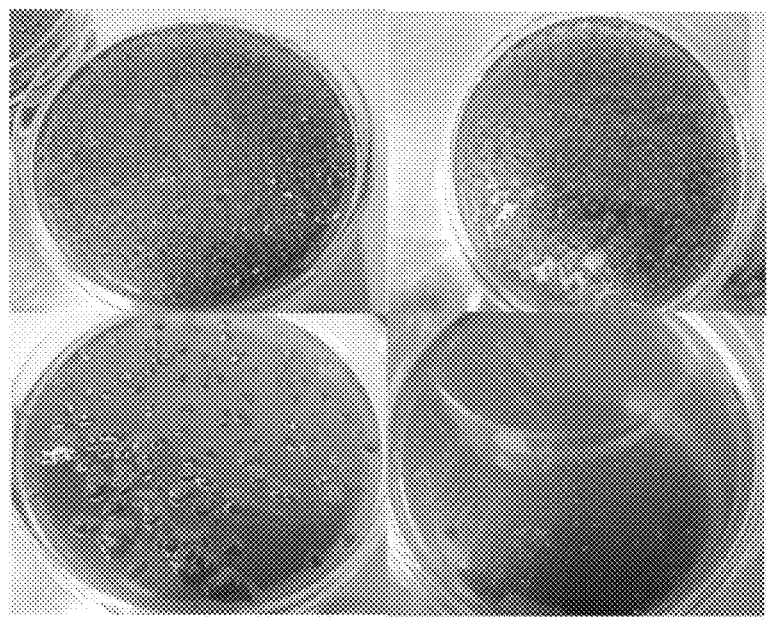
FIG. 9 shows the blue colonies of S. mutans after the completion of incubation period and staining.

According to FIG. 7 to prepare the Mitis Salivarius Agar culture medium (Quelab, UK), 90 g of culture medium powder and 200 g of sucrose (Merck, Darmstadt, Germany) were dissolved in 1 L of distilled water and autoclave-sterilized at 110° C. and 15 ibs/in$^2$ pressure for 15 min. After cooling to 50° C., 1 mL/L of 1% potassium tellurite (Merck, Darmstadt, Germany) and 0.2 µ/mL of bacitracin stock solution (previously sterilized by a syringe filter) were added to the culture medium. After mixing, 25 mL of culture medium was poured into sterile plates.

Samples transferred to the microbiology lab were centrifuged and 10 serial dilutions were prepared using sterile serum. Of each dilution, 0.1 unit/mL was streak-cultured on Mitis Salivarius Agar culture medium. The culture plates were then incubated at 37° C. for 48 h. To ensure that the counted colonies were S. mutans colonies, they were Gram-stained and catalase and Voges-Proskauer tests were also performed. Gram-staining revealed chains of Gram-positive cocci.

The bacteria could not break down hydrogen peroxide and the catalase test result was negative. The Voges-Proskauer test result was positive and color change was observed. Thus, after the completion of incubation period and staining, the prominent, granulated, blue colonies of *S. mutans* were counted. In order to obtain the total number of bacteria present in the original sample, the number of counted colonies at each concentration was multiplied by the inverse of the dilution factor. Number of colony forming units per milliliter (CFUs/mL)=number of colonies/(transferred volume×dilution factor) OR number of colonies×inverse of the dilution factor ($10^{-4}$)×inverse of the transferred volume (0.1 mL)

Data were analyzed using SPSS version 25 (SPSS Inc., IL, USA). Normality of the data was evaluated using the Kolmogorov-Smirnov test. The Mann Whitney test was used to compare the salivary colony count between the two groups at different time points. The Friedman test was used to compare the colony count in the saliva samples separately in each group at 7, 14, 21 and 28 days. The Wilcoxon test was used to analyze the difference in salivary colony count at different time points. The Mann Whitney test was applied to compare the bacterial colony count in plaque samples between the two groups at different time points. The Wilcoxon test was applied to analyze the difference in bacterial count in plaque samples in each group at different time points. The bacterial colony count on elastomeric ligature samples was compared between the two groups at different time points using the Mann Whitney test.

Tables 1, 2 and 3 show the salivary count of *S. mutans*. The Kolmogorov-Smirnov test revealed that data were not normally distributed in the test and control groups ($P<0.05$). Thus, non-parametric tests were applied for data analysis.

TABLE 1

Salivary count of *S. mutans* at baseline and at 7, 14, 21 and 28 days after the intervention

| Time point | Control group | | Test group | | |
|---|---|---|---|---|---|
| | Mean | Std. deviation | Mean | Std. deviation | P value |
| Baseline | 1.08 | 0.49 | 1 | 0.55 | 0.78 |
| 7 days | 1.07 | 0.42 | 0.69 | 0.48 | 0.037 |
| 14 days | 1.14 | 0.47 | 0.39 | 0.32 | <0.001 |
| 21 days | 1.13 | 0.55 | 0.21 | 0.21 | <0.001 |
| 28 days | 1.23 | 0.61 | 0.13 | 0.12 | <0.001 |

*The mean and std. deviation values are based on $10^5$ CFUs.

Table 1 presents the salivary count of *S. mutans* at baseline and at 7, 14, 21 and 28 days after the intervention. The Mann-Whitney test revealed no significant difference in salivary count of *S. mutans* between the test and control groups at baseline ($P=0.78$). However, the salivary count of *S. mutans* started to increase in the control group and started to decrease in the test group during the course of study. The salivary count of *S. mutans* was significantly lower in the test group at 7, 14, 21 and 28 days ($P<0.05$).

Friedman test was then applied within-group comparisons. It revealed no significant difference in salivary count of *S. mutans* in the control group during the one-month study period ($P=0.061$). However, this difference was significant in the test group ($P<0.001$). Wilcoxon test was then applied to analyze the difference in salivary count of *S. mutans* at different time points in the two groups. In the control group, the difference in this regard was not significant between different time points ($P>0.05$, Table 2). However, a significant reduction in *S. mutans* colony count was noted over time in the test group.

TABLE 2

Results of Wilcoxon test for pairwise comparisons of salivary *S. mutans* colony count at different time points

| Time | Control group | Test group |
|---|---|---|
| Baseline-7 days | 0.865 | 0.001 |
| 7 days-14 days | 0.363 | 0.001 |
| 14 days-21 days | 0.691 | 0.001 |
| 21 days-28 days | 0.105 | 0.004 |
| Baseline-28 days | 0.088 | 0.001 |

Table 3 shows the *S. mutans* count in dental plaque samples collected at baseline and at 28 days (Table 3). The Mann Whitney test was used to compare the plaque *S. mutans* count of the two groups, which revealed no significant difference between the test and control groups in this respect ($P>0.05$). Wilcoxon test revealed no significant increase in colony count in dental plaque at 28 days compared with baseline in the control group ($P=0.910$). In the test group, no significant reduction was noted in *S. mutans* colony count at 28 days compared with baseline ($P=0.081$).

TABLE 3

*S. mutans* colony count in dental plaque samples collected at baseline and at 28 days

| | Control group | | Test group | | |
|---|---|---|---|---|---|
| | Mean | Std. deviation | Mean | Std. deviation | P value |
| Baseline | 1.1 | 0.47 | 1 | 0.54 | 0.425 |
| 28 days | 1.11 | 0.51 | 0.97 | 0.54 | 0.400 |

*The mean and std. deviation values are based $10^5$ CFUs.

The mean count of *S. mutans* on elastomeric ligature samples was 0.51±0.48 (×$10^5$) CFUs in the test and 1.02±0.50 (×$10^5$) CFUs in the control group at 28 days. The Mann Whitney test revealed a significant difference in this respect between the two groups ($P=0.003$).

The results showed that the salivary count of *S. mutans* was significantly lower in the test group at 7, 14, 21 and 28 days ($P<0.05$). The *S. mutans* count on the surface of CHX-releasing ligatures was significantly lower than that on the surface of conventional ligatures ($P<0.05$). However, no significant difference was noted in *S. mutans* count in plaque samples between the two groups ($P>0.05$). The salivary level of *S. mutans* significantly decreased during the course of study in the test group.

In this clinical study, the patients were asked not to use fluoride- or CHX-containing gels or mouthwashes during the study period to prevent their confounding effects on the results. None of the patients showed any side effect related to the use of CHX, which is probably due to the use of relatively low concentration of CHX in the coating.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

With respect to the above description, it is to be realized that the optimum relationships for the parts of the invention in regard to size, shape, form, materials, function and manner of operation, assembly and use are deemed readily apparent and obvious to those skilled in the art, and all equivalent relationships to those illustrated in the drawings and described in the specification are intended to be encompassed by the present invention.

REFERENCES

1. Mašek I, Matošević D, Jurić H, Meštrović S. Antimicrobial effects of chlorhexidine in orthodontic patients. Acta stomatologica Croatica. 2008 Mar. 15; 42(1):41-8.
2. Twetman S, Hallgren A, Petersson L G. Effect of an antibacterial varnish on mutans streptococci in plaque from enamel adjacent to orthodontic appliances. Caries research. 1995; 29(3):188-91.
3. Tang X, Sensat M L, Stoltenberg J L. The antimicrobial effect of chlorhexidine varnish on mutans streptococci in patients with fixed orthodontic appliances: a systematic review of clinical efficacy. International journal of dental hygiene. 2016 February; 14(1):53-61.
4. Lipták L, Szabó K, Nagy G, Márton S, Madléna M. Microbiological changes and caries-preventive effect of an innovative varnish containing chlorhexidine in orthodontic patients. Caries research. 2018; 52(4):272-8.
5. Miura K K, Ito I Y, Enoki C, Elias A M, Matsumoto M A. Anticariogenic effect of fluoride-releasing elastomers in orthodontic patients. Brazilian oral research. 2007 Sep.; 21(3):228-33.
6. Benson P E, Douglas C I, Martin M V. Fluoridated elastomers: effect on the microbiology of plaque. American journal of orthodontics and dentofacial orthopedics. 2004 Sep. 1; 126(4325-30.
7. Jeon H S, Choi C H, Kang S M, Kwon H K, Kim B I. Chlorhexidine-releasing orthodontic elastomerics. Dental materials journal. 2015 May 28:2014-16.
8. Jeon H S, Jung E H, Kang S M, Lee E S, Lee J W, KIM B I. Improving the efficacy of chlorhexidine-releasing elastomerics using a layer-by-layer coating technique. Dental materials journal. 2017 Jul. 25; 36(4):476-81.
9. Chung S H, Cho S, Kim K, Lim B S, Ahn S. J. Antimicrobial and physical characteristics of orthodontic primers containing antimicrobial agents. The Angle Orthodontist. 2016 Sep. 6; 87(2):307-12.

What is claimed is:

1. A method for production of anti-microbial orthodontic elastomeric ligatures, comprising the steps of:
   a) preparing a coating solution by mixing an anti-bacterial agent, a polymer and a solvent by a ratio of 2 g anti-bacterial agent, 4 g polymer and 200 mL solvent;
   b) selecting a hypo-allergic latex-free orthodontic elastomeric ligatures with an internal diameter of 0.045 inches and external diameter of 0.115 inches;
   c) rinsing said hypo-allergic latex-free orthodontic elastomeric ligature in distilled water and drying at 60° C.;
   d) spraying the anti-bacterial on the hypo-allergic latex-free orthodontic elastomeric ligature two times and drying for five minutes;
   e) repeating step (d) five times, and
   f) drying the elastomeric ligature at room temperature for 1 h.

2. The method of claim 1, wherein the anti-bacterial agent is chlorhexidine (CHX) diacetate.

3. The method of claim 1, wherein the polymer is ethyl cellulose.

4. The method of claim 1, wherein the solvent is dichloromethane.

* * * * *